(12) United States Patent
Laxhuber

(10) Patent No.: US 8,594,782 B2
(45) Date of Patent: Nov. 26, 2013

(54) APPARATUS AND METHODS FOR DETERMINING THE LOCATION OF THE APEX OF A DENTAL ROOT CANAL

(75) Inventor: Ludwig Laxhuber, Herrsching (DE)

(73) Assignee: Endosafe GmbH, Bregenz (AT)

( * ) Notice: Subject to any disclaimer, the term of this patent is extended or adjusted under 35 U.S.C. 154(b) by 0 days.

(21) Appl. No.: 13/521,537

(22) PCT Filed: Sep. 10, 2010

(86) PCT No.: PCT/EP2010/005571
§ 371 (c)(1),
(2), (4) Date: Aug. 16, 2012

(87) PCT Pub. No.: WO2011/085742
PCT Pub. Date: Jul. 21, 2011

(65) Prior Publication Data
US 2012/0322027 A1 Dec. 20, 2012

(30) Foreign Application Priority Data
Jan. 14, 2010 (EP) .................................. 10000306

(51) Int. Cl.
*A61B 5/00* (2006.01)
(52) U.S. Cl.
USPC ........................................................ 600/547

(58) Field of Classification Search
USPC ................ 600/547, 590; 33/513; 433/72, 224
See application file for complete search history.

(56) References Cited

U.S. PATENT DOCUMENTS

| 5,080,586 | A | 1/1992 | Kawai |
| 5,759,159 | A | 6/1998 | Masreliez |
| 6,520,775 | B2* | 2/2003 | Lee ................................ 434/263 |
| 6,845,265 | B2* | 1/2005 | Thacker ........................ 600/547 |
| 7,909,604 | B2* | 3/2011 | Shoji et al. ...................... 433/72 |
| 8,348,863 | B2* | 1/2013 | Gamba et al. .................. 600/590 |
| 8,388,340 | B2* | 3/2013 | Crohn et al. ..................... 433/72 |
| 2002/0055085 | A1 | 5/2002 | Perdomini |

FOREIGN PATENT DOCUMENTS

| DE | 102008038505 A1 | 5/2009 |
| EP | 0392518 A1 | 10/1990 |
| WO | 2008/155751 A1 | 12/2008 |

* cited by examiner

Primary Examiner — Max Hindenburg
(74) Attorney, Agent, or Firm — McDonnell Boehnen Hulbert & Berghoff LLP

(57) ABSTRACT

The invention relates to the field of medical methods and equipment and in preferred embodiments to equipment and methods used in dentistry. In particular it relates to an apparatus for determining the location of the apex of a dental root canal wherein the apparatus allows the acquisition of more accurate data in a shorter time span.

13 Claims, 7 Drawing Sheets

In the example shown in Fig. 2-4:

| | |
|---|---|
| γ: | 0,06 |
| ß: | 0,3 |
| u: | 5 |
| $w_o$ | 500 |
| C | 0,0000001 |
| $R_o$ | 9700 |
| n | -1 |

$w_\gamma(t) = w_o(1+\gamma t)^n$ $w_\beta(t) = w_o(1+\beta t)^n$ $Rc_\beta = 1/(w_\beta * C)$ $Rc_\gamma = 1/(w_\gamma * C)$ $R_\beta = R_o * Rc_\beta / (R_o + Rc_\beta)$ $R_\gamma = R_o * Rc_\gamma / (R_o + Rc_\gamma)$ $\Delta R = |R_\gamma - R_\beta|$

| | |
|---|---|
| ΔRmax (approx.) | 1210 |
| Δtmax (approx.) | 11 |

Different rates ß=γu' with u': 5u, u, u/5

(γ=2, u=5.83, $\Delta R_{max}$= 25 kΩ)

APPARATUS AND METHODS FOR DETERMINING THE LOCATION OF THE APEX OF A DENTAL ROOT CANAL

FIELD OF THE INVENTION

The invention relates to the field of medical methods and equipment and in preferred embodiments to equipment and methods used in dentistry. In particular it relates to an apparatus for determining the location of the apex of a dental root canal wherein the apparatus allows the acquisition of more accurate data in a shorter time span.

BACKGROUND OF THE INVENTION

In root canal therapy, the interior of a root is removed prior to filling the root with replacement material. If the canal is not completely emptied of the root material prior to filling with the replacement material, leftover root material can retard healing and even act as a focus for infection. For this reason, all of the natural interior material in the root is removed before filling.

Both mechanical and chemical means are used to eliminate such germs in the root canal in an effort to prevent further infection. Traditionally this has been done using a mechanical means such as a reamer or a file. Also, the root canal should be fully closed almost all the way to its apical foramen so as to completely prevent a recurring infection. Accordingly, it is essential to accurately determine the position of the end of the root canal, known also as the apical foramen. In order to measure the length of the root canal, different methods have heretofore been used. In general it is conventional to insert a probe into the excavated root canal and to determine how far the tip of the probe is from the apex of the root.

This method may comprise, e.g. determining by hand when a probe such as a file or reamer is in contact with the apical foramen, taking an X-ray with said probe inserted in the root canal, or also electrically detecting the apical foramen by means of impedance variations. Once the apex of the tooth has been determined, a mechanical cutter such as a hand-operated reamer or file, or an engine reamer or ultrasonic cutter, is then frequently used to enlarge and clean the root canal.

It is, however, difficult even for a skilled dentist to efficiently perform such a series of operations, which are time-consuming and may cause patients to suffer severe pain.

Different prior art systems have been devised to accelerate this method. In one prior art system, which is based on an impedance measurement, an electrical measuring means has an alternating power source with a frequency of 200 Hz. When the reamer reaches the apical foramen, the value of a voltage is measured. This clinically pre-determined value is then used as a reference value indicating when the reamer has reached the apical foramen for future measurements. In another system, developed for detecting any given position in the root canal by means of impedance differential, voltages are used that have two different fixed frequencies, for example, 1 kHz and 5 kHz. Waveforms of those frequencies are superposed to provide a composite or voltage waveform. In this system (see U.S. Pat. No. 5,080,586, the disclosure of which is incorporated herein by reference), the apex is located by electrification of the probe with applied pulses at two different fixed frequencies and measuring a current flowing between the probe and an electrode at the gum of the patient. The measured current is filtered to provide only the fundamental frequency to an apex location determination circuit. The changes in the two filtered signals is compared as the probe moves along the root canal and resulting changes in the current values are used to determine the apex location. This current is measured by measuring the voltage on a resistor situated between the gum electrode and ground.

The aforementioned prior art systems, however suffer from an insufficient signal sensitivity especially when the probe is in close proximity of the tooth apex. To overcome these deficiencies, the present invention provides an improved system with an improved signal to noise ratio and, thus, an improved accuracy as compared to prior art methods. Thus, a more accurate determination of the apex in a shorter time span becomes possible.

SUMMARY OF THE INVENTION

To solve the aforementioned problems and to provide an improved means for obtaining fast and accurate results during the measurement of the distance between a probe and the apical foramen of a tooth the invention provides in a first aspect an apparatus for determining the location of the apex of a root canal of a tooth, wherein the apparatus comprises the following components:
(a) a first electrode shaped to be insertable into the root canal of a tooth of a patient and a second electrode which is shaped to be placed in contact with another body part of said patient, preferably with the oral mucosa or with a hand of said patient;
(b) a frequency sweep generator capable of generating a succession of at least four voltage signals with different frequencies between the first and the second electrode;
(c) a measuring device capable of measuring the impedances between the first and the second electrode corresponding to the voltage signals generated by said frequency sweep generator;
(d) a computing unit, capable of controlling the voltage signals generated by the frequency sweep generator, capable of reading the respective impedance values from the measuring device and capable of computing the distance between said first electrode and said tooth apex from said impedance values; and
(e) optionally an output device capable of outputting said computed distance.

Also provided in a second aspect is a method for determining the location of the apex of a dental root canal, wherein the method comprises the following steps:
(a) providing a first electrode that is located in the root canal of a tooth of a patient and a second electrode which is in contact with another body part of said patient, preferably with the oral mucosa or with a hand of said patient;
(b) carrying out a first fast frequency-sweep comprising:
obtaining a first series of at least four electrical impedance measurements using the first and the second electrode and using frequencies selected from a frequency of between 10 Hz and 40 kHz, while noting for each individual impedance measurement at which point in time it was taken;
(c) carrying out a second slower frequency-sweep comprising:
(i) obtaining a second series of at least four electrical impedance measurements using the first and the second electrode and using essentially the same frequency range as defined in step (b) but measuring the individual impedance measurements in slower succession than in step (b), while noting for each individual impedance measurement at which point in time it was taken; or (ii) extrapolating the impedance measurements of the second slow frequency-sweep from the impedance data-set obtained in step (b);

(d) comparing the impedance data-set obtained in step (b) with the impedance data-set obtained in step (c) to determine $t_{max}$ and $\Delta R_{max}$, wherein $t_{max}$ is the common time point in both frequency sweeps at which the impedance difference $\Delta R_{max}$ between an impedance measured at or corresponding to $t_{max}$ in step (b) and an impedance measured at or corresponding to $t_{max}$ in step (c) is largest; and (e) determining the distance x between the apex of said dental root canal and said first electrode using the determined $t_{max}$ and $\Delta R_{max}$ values.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, is hereby incorporated by reference in its entirety. Nothing herein is to be construed as an admission that the invention is not entitled to antedate such disclosure by virtue of prior invention.

A "patient" in the sense of the present application may be any animal to which the apparatus of the invention can advantageously be applied. As such, a "patient" may be any animal. In more preferred embodiments, a "patient" is a mammal. In especially preferred embodiments, a patient is a horse, a donkey, cattle, a sheep, a goat, a pig, a dog, a cat, or, in particular, a human.

As used herein "curve fitting" means obtaining a curve that best fits to the mentioned values, e.g. impedance values. Curve fitting is the process of constructing a curve, or a mathematical function, that has the best fit to a series of data points. Curve fitting can involve e.g. an interpolation of the data or smoothing, in which a "smooth" function is constructed that approximately fits the data. For the purpose of the present invention an algebraic fit or a geometric fit can be used. The curve can also be fitted to the data points using a polynomial function. Thus, as is well known in the art, many possible curve fitting methods are available, all of which may be used. Preferred fits comprise interpolation and fitting a polynomial function to the values.

The term "dielectric" refers to a material which essentially does not conduct electrical current, i.e. it refers to any insulating substance a plurality of which are known in the art.

The phrase "frequency sweep" as used throughout this specification refers to generating a succession of (preferably at least four) voltage signals with different frequencies. During a sweep, the respective voltage signal frequencies are varied in any order. Thus, during a frequency sweep, the frequency of each voltage signal may be increasing or decreasing over time within a given frequency range. Increasing or decreasing frequencies are preferably chosen such that the increase or decrease is constant (i.e. linear) or non-linear over the sweep. Preferred embodiments of selecting the frequencies for the first and/or second frequency sweep (i.e. for said at least four voltage signals, respectively) are provided further below.

It is preferred that a "frequency sweep" as referred to herein comprises more than 10, 15, 20, 25, 30, 40, 50, 60, 70, 80, 90, 100, 120, 140, 160, 180, 200, 250, 300, 350, 400, 450, 500 or even more different frequencies.

In preferred embodiments of a first and/or second frequency sweep a non-linear succession of frequencies may be selected for the voltage signals to be generated.

The present invention provides an apparatus that offers greater precision in the determination of the apex location of a tooth since during measurement an optimal signal to noise ratio is achieved by applying an enhanced frequency sweep method (see also examples below).

Specifically, the invention provides in a first aspect, an apparatus for determining the location of the apex of a root canal of a tooth, wherein the apparatus comprises the following components:

(a) a first electrode insertable into the root canal of a tooth of a patient and a second electrode which is shaped to be placed in contact with another body part of said patient, preferably with the oral mucosa or with a hand of said patient;

(b) a frequency sweep generator capable of generating a succession of at least four voltage signals with different frequencies between the first and the second electrode;

(c) a measuring device capable of measuring the impedances between the first and the second electrode corresponding to the voltage signals generated by said frequency sweep generator;

(d) a computing unit, capable of
controlling the voltage signals generated by the frequency sweep generator;
reading the respective impedance values from the measuring device; and
capable of computing the distance between said first electrode and said tooth apex from said impedance values; and (e) optionally an output device capable of outputting said computed distance.

The measuring device will preferably measure for each generated voltage signal the corresponding impedance (which also may be a voltage reading as is further outlined herein). A voltage signal is in a preferred embodiment a voltage waveform that is supplied to said first electrode via a resistor using a power supply preferably coupled to an oscillator as also described herein.

Preferred first electrodes that can be used in the apparatus of the invention include elongated and preferably cylindrical electrodes. In one embodiment, the first electrode is a needle or reamer electrode having a length of between 10 mm and 50 mm. Preferably, the first electrode used according to the invention is elongated and has a length of not more than 10 mm, 12 mm, 14 mm, 16 mm, 18 mm, 20 mm, 25 mm, 30 mm or not more than 35 mm. The first electrode must be made from a material that is an electrical conductor. Thus, in one preferred embodiment the first electrode is made of stainless steel, surgery steel, copper, silver or mixtures thereof. Further preferred are elongated first electrodes such as needle electrodes that have a diameter of between 0.1 mm and 0.5 mm preferably between 0.1 to 0.25 mm, e.g. about 0.1 mm, 0.15 mm, 0.2 mm or 0.25 mm. In one preferred embodiment, the first electrode is elongated and the tip of the elongated electrode is configured as a bead with a diameter of between 0.2 mm and 1.0 mm, preferably of between 0.4 mm and 0.6 mm and most preferably of about 0.5 mm.

In a preferred embodiment, the frequency sweep generator of the apparatus according to the invention comprises an oscillator and optionally an attenuator. Electronic devices for measuring an apex location in a tooth by determining the electrical impedance between two electrodes one of which is inserted into the tooth canal have been described in detail (see e.g. US Patents U.S. Pat. Nos. 5,080,586 B1 and 6,482,008 B2 and European patent EP 0 392 518 B1) and, thus, the average skilled person is able to construct the apparatus of the invention based on the aforementioned information and also using the information provided herein.

Preferably, said measuring device of the apparatus of the invention comprises or consists of an amplifier for amplifying a voltage waveform measured between said first and second electrode.

In a further preferred embodiment, said measuring device of the apparatus of the invention comprises or consists of a rectifier for rectifying the measured voltage waveform.

Also preferred is the apparatus of the invention, wherein said computing unit comprises hardware capable of carrying out a method which comprises the following steps:
(i) carrying out a first frequency-sweep at a frequency rate $\gamma$ and recording for each generated voltage signal the respective impedance value and time point of the impedance measurement; and
(ii) determining the distance between said first electrode and said tooth apex from the impedance values recorded in (i).

In one embodiment, said hardware may be a computer program running on a computer with interfaces to said frequency sweep generator, said measuring device and, optionally said output device.

Said computing unit of the apparatus of the invention does not necessarily be physically separated from the frequency sweep generator and/or measuring device but may also be an integral part thereof.

Said frequency rates $\gamma$ and $\beta$ (see below) define how fast the respective frequency sweep is carried out. As mentioned above and below, a frequency sweep may be linear or non-linear. Furthermore, a sweep may go from a high frequency to a lower frequency or vice versa. Preferred embodiments of how to select individual frequencies using $\beta$ and $\gamma$ are described below and also in the examples.

As is known to the average skilled person, various methods for measuring impedance are available in the art. Accordingly, an "impedance value" or "impedance" as used herein generally refers to a measure of opposition to alternating current (AC). In one example, the impedance of a device can be calculated by applying a sinusoidal voltage to the device in series with a resistor, and measuring the voltage across the resistor and across the device. For the purpose of this invention a measured impedance value can be used directly or also transformed into any measure which correlates with the impedance, e.g. the relative amplitudes of the voltage and current measured.

"Recording" of the measured impedance values can e.g. occur in form of a print out and/or in electronic form, for example the values are stored on a storage device such as a hard disk, RAM, ROM, an EEPROM (for example flash memory) and/or EPROM memory.

In one embodiment, said "computing unit" may have the form of an integrated circuit. Such integrated circuit may in a preferred embodiment also be implemented as an application-specific integrated circuit (ASIC), as is well known in the art of integrated circuit design.

Said output device (see also step 120 in FIG. 6) may communicate to the dentist the determined apex location, i.e. said distance x between the apex of said dental root canal and said first electrode by various means known in the art, including by acoustic and/or optic means such as but not limited to sound signals, light flashes, LED displays, flat panel displays, electroluminescent displays (ELD), plasma display panels (PDP), liquid crystal displays (LCD), HPA displays, thin-film transistor displays (TFT), organic light-emitting diode displays (OLED) and surface-conduction electron-emitter displays (SED).

Thus, the apparatus of the invention determines the distance between said first electrode and said tooth apex using the measured and optionally recorded impedance values obtained in a frequency sweep. The distance x (i.e. the distance between said first electrode and said tooth apex) can in a preferred embodiment of the apparatus be obtained by:
fitting a first curve through the impedance values obtained from the first frequency sweep, wherein said first curve defines which time points during the first frequency sweep correlate with which respective impedance value of the first sweep; and
correlating the curve or a derivative thereof with said distance x between the apex of said dental root canal and said first electrode.

The advantage of using a fitted curve rather than discrete individual impedance measurements is that the distance x can be determined more accurately, as a plurality of individual experimental measurements are more accurately defined by a single curve fitted to these measurements. Thus, curve characteristics, such as e.g. the area under the curve, preferably only the area under the section of the curve within the sweep duration, the mean and/or the median of the curve, are preferably correlated to the distance x. Also other more preferred curve characteristics can be used, as will be outlined below. As the measured impedances will correlate to the distance x, the distance x can be computed in one embodiment by multiplication of the curve characteristic/property as outlined herein with a predetermined factor. For example, a lookup table may be used comprising clinically determined values of x and the respective values of the resultant curves. Thus, in a preferred embodiment, the apparatus of the invention is equilibrated by correlating a curve characteristic with the actual physically determined distance x (which in one example can be determined using x-ray methodology as is well known in the art). Typically a series of frequency sweeps will be carried out, each series taken at a different distance x once using the apparatus of the invention and once using a different method of determining the actual distance x (e.g. by using x-ray images). Generally, the closer the first electrode will be to the tooth apex the smaller the measured impedances will become and if the impedance is expressed as a voltage then the larger this voltage will become (due to the low impedance value—see also e.g. FIG. 3 of EP 0 392 518 A1). Thus, by way of correlation, a formula can be found, or alternatively a lookup table can be established as mentioned above that will allow to correlate a determined curve characteristic with the actual distance x. Alternatively, the distance between the needle electrode and the tooth apex can also be computed e.g. using the formulas provided in example 1 below. Thus, in one preferred embodiment, the computing unit of the apparatus of the invention computes the distance between said first electrode and said tooth apex by:

(a) obtaining a curve that is fitted to said impedance values obtained from said first and/or second frequency sweep (see also e.g. step 110 of FIG. 6); and
(b) using a feature of said curve obtained in (a) selected from the group consisting of the area under the curve, the mean of the curve, the median of the curve, the derivative of the curve and curve properties including obtaining a second and third curve as described herein below and combinations thereof to determine said distance x preferably by using a look-up table or a predetermined calibration factor such as described herein.

In the following, a preferred method of determining a curve characteristic will be described by obtaining a second and a third curve as outlined in the following:

In a preferred embodiment of the apparatus according to the invention step (ii) as outlined above comprises the following further steps:

(iii) fitting a first curve to the impedance values obtained from the first frequency sweep, wherein said first curve defines which time points during the first frequency sweep correlate with which respective impedance values of the first sweep (i.e. the curve defines the measured (or fitted) impedance values over time);
(iv) carrying out a second frequency-sweep at a frequency rate $\beta$, which is different and preferably smaller than the frequency rate $\gamma$, analogous to (i) or by extrapolating the impedance and time point values from the first curve obtained in (iii) (see also step 200 of FIG. 7);
(v) fitting a second curve through the impedance values obtained from the second frequency sweep, wherein said second curve defines which time points during the second frequency sweep correlate with which respective impedance values of the second frequency sweep (see also step 210 of FIG. 7);
(vi) obtaining a third curve which is the (preferably absolute) difference between the first and the second curve;
(vii) finding the maximum of the third curve which is the maximal impedance difference $\Delta R_{max}$ recorded at the time point $t_{max}$; and optionally determining the area F under the third curve between t=0 and t=$t_{max}$ (see also step 230 of FIG. 7); and
(viii) determining the distance x between the apex of said dental root canal and said first electrode using the determined $t_{max}$ and $\Delta R_{max}$ values and optionally the F value.

In this context "extrapolating" means that the second curve is obtained by computation and not by an actual measurement. For the extrapolation (see also FIG. 7), the first curve obtained in (iii) is preferably resealed in the time axis by rescaling the time values without rescaling the recorded impendence values. Thus, the second curve is preferably obtained using the impedance-values of said first curve multiplied by a factor which is a real value that is preferably not 1 and most preferably greater than 1. An exemplary first ($R_\beta$) and second ($R_\gamma$) impedance curve obtainable using the apparatus of the invention is also shown in FIG. 3 below.

In a further preferred embodiment of the apparatus of the invention the apparatus is configured to carry out the same number of impedance measurements during the first and the second frequency sweep.

The inventors have determined optimal frequency ranges that can be used to carry out the first and/or second frequency sweep.

In one embodiment of the apparatus, the frequencies used in the first and/or second frequency sweep are selected from the frequency range comprising the frequencies between 10 Hz and 40 kHz and more preferably comprising the frequencies between 14 Hz and 10 kHz.

As used herein "frequency range" refers to a range of frequencies over which the first and/or second frequency sweep is carried out. Thus, said at least four frequencies used in the sweep carried out by the apparatus of the invention will be selected from such frequency range. The range is defined by a minimum and maximum frequency. Preferred minimum and maximum frequencies of preferred frequency ranges are mentioned throughout this specification. It is preferable, however, that the maximum frequency of a frequency range for the purpose of the present invention does not exceed 40 kHz since above this frequency dampening of the voltage signal (frequency pulse) may occur.

Preferably, the apparatus will be configured such that at least 4, 5, 6, 7, 8, 9 or at least 10, more preferably at least 50 and most preferably at least 100 voltage signals with different frequencies are generated during the first and/or second frequency-sweep and the respective impedance measurements are taken. The number of measurements can also be adapted to the frequency range used in the apparatus of the invention. For larger frequency ranges it is preferable to use a larger number of measurements.

For example, if the apparatus of the invention is configured so that said first frequency sweep is carried out e.g. using a frequency range of 500 Hz to 40 kHz then the sweep can, in one example, comprise 790 measurements. Preferably, also for the reasons outlined below, these measurements are taken in a time interval of less than 0.6, less than 0.5, less than 0.4, less than 0.3, less than 0.2 or most preferably, in less than 0.1 seconds, i.e. the first and/or second frequency sweep will preferably be completed in the aforementioned preferred time span.

A tremor is an involuntary movement or shaking of any body part. It is often also noticeable in the hands. Physiological tremor is generally a very-low-amplitude fine tremor that is barely visible to the naked eye. It is present in every normal individual during maintaining a posture or movement. Fatigue (e.g. rigid muscles), low blood glucose levels, caffeine intake and many other factors influence the frequency and amplitude of fine tremors. If a physician measures the location of a tooth apex, the naturally occurring hand tremor may slightly influence the location of the probe. Thus, it will be advantageous to complete the determination of the apex location in a small amount of time. This will also allow taking multiple readings of the distance x for each needle position. In a preferred embodiment of the apparatus of the invention, multiple measurements of the apex location, e.g. two, three or four individual measurements of x are averaged before outputting the averaged distance x value.

Thus, in a preferred embodiment of the apparatus of the invention the first and/or second frequency-sweep is completed in less than 0.6, less than 0.5, less than 0.4, less than 0.3, less than 0.2 or most preferably, in less than 0.1 seconds.

If one assumes in one example that the measurement of a single voltage signal with a given frequency takes 2 µs, then this can be used as a basis to calculate how many impedance measurements may maximally be taken. For example, if a single impedance measurement takes 2 µs and the first frequency sweep is to be completed in 0.1 seconds, then this would allow for 50 impedance measurements. Thus, in a preferred embodiment, the apparatus of the invention is configured such that the first frequency sweep comprises measuring impedance values for not more than 50 different frequencies. Thus, in one embodiment of the apparatus, 4-50 frequencies are used during the first frequency sweep and these frequencies are preferably, as has also been outlined above, selected from a frequency range comprising the frequencies between 10 Hz and 40 kHz and more preferably comprising the frequencies between 14 Hz and 10 kHz.

Furthermore, as will be appreciated from the examples provided herein below, in order o be able to determine $\Delta R_{max}$, it will only be necessary to carry out the first frequency sweep up to the time point $t_{max}$. Thus, in a preferred embodiment of the method of the invention, the frequency rates (sweep rates) $\beta$ and $\gamma$ are selected such that $t_{max}$ becomes smaller or equal than 0.6 seconds and preferably less than 0.1 seconds.

In a further preferred embodiment of the apparatus of the invention, the second frequency-sweep is carried out by selecting the frequencies according to the following formula:

$$w_\beta(t) = w_o(1+\beta t)^n;$$

wherein t is the time, $w_\beta(t)$ is the time-dependent frequency function, $w_o$ is the starting frequency of the sweep, $\beta$ is the frequency rate (e.g. the rate by which the frequencies are increased or decreased during the first sweep), and n is any real number describing the relation between $w_\beta(t)$ and t and resulting in different curve forms $w_\beta(t)$, for example:

n=1: results in a linear relation between w and t: $w_\beta(t)=w_o(1+\beta t)$ n=0: results in the known case of a constant frequency: $w_\beta(t)=w_o$ n=−1: results in an inverse relation between w and t, which will be often used as an example: $w_\beta(t)=w_o/(1+\beta t)$.

For other specific measurement requirements a different specific n may be more appropriate. Preferably, n is not 0 as this will not provide alternating frequencies.

Also preferred is an apparatus of the invention, wherein the first frequency-sweep is carried out by selecting the frequencies according to the following formula:

$$w_\gamma(t) = w_o(1+\gamma t)^n;$$

wherein t is the time, $w_\gamma(t)$ is the time-dependent frequency function, $w_o$ is the starting frequency of the sweep, $\gamma$ is the frequency rate (e.g. the rate by which the frequencies are increased or decreased during the second sweep), and n is any real number, preferably not zero.

As shown in the examples, the measurement of the distance x is especially reliable, when an optimized ratio between the frequency rates $\beta$ and $\gamma$ is selected. Thus, in one preferred embodiment of the apparatus of the invention, the sweep rates $\beta$ and $\gamma$ are selected such that the ratio $u=\beta/\gamma$ is a value between 4 and 8 and more preferably between 5 and 7. In a most preferred embodiment the ratio u is selected such that u=5.83.

In one embodiment of the apparatus of the invention, said second electrode is a lip electrode capable of contacting the oral mucosa of the patient and/or is a hand-held electrode. It is preferred that the second electrode has a contact (preferably planar) surface area of between 1 cm² and 5 cm².

Furthermore, the apparatus of the invention preferably comprises a handle (50) (an example of which is partially shown in FIG. 1) made from a dielectric and configured to hold said first electrode which is shown in a preferred embodiment as needle or reamer electrode (15) in FIG. 1. In one embodiment, the handle (50) is made of insulating material and includes an electrically conducting metal core (3) for contact with the first electrode (15). The length of said handle is substantially 100 mm, with a preferred diameter of 12 mm in the head (5) into which can be inserted the haft (1) of the needle (15) as seen in FIG. 1. An assortment of needles/reamers is provided comprising various lengths, but the average preferred length is about 30 mm. Their shape is generally tapered, diameter varying from about 0.25 mm at the base to about 0.1 mm at the tip (FIG. 1). In one embodiment, the first and/or second electrode may be made of stainless steel. The diameter of the haft (1) for the first electrode is preferably about 1 mm, the length of the rear section (2) preferably being about 15 mm and that of the front section (4) preferably about 5 mm. The fore end is preferably bent at an angle of about 110° compared with the rear end.

Assuming that a tooth (7) with a root infection has to be treated, generally an anaesthetic will be administered and an aperture (6) of a diameter of 2-4 mm is made into the crown to provide access to the root canal (14) (FIG. 1). Said canal is then probed to calculate the necessary depth which should correspond to the entire length of the canal less about 1 mm from its apex. Said tooth canal will have an anatomical apex (8) and a radiological apex (12) as shown in FIG. 1. A bundle of nerves (10), at least one artery (11) and veins (9) will enter said root canal at the apical foramen of the tooth (see FIG. 1). By using said first electrode (15) with the apparatus of the invention it is possible to calculate the distance between the apex of the tooth and the tip of said needle electrode by electronic means as described herein. While the first electrode is advanced towards the tooth apex, this distance is preferably repeatedly determined using the apparatus of the invention to allow the operator to stop the needle at the correct position which is preferably 1.5 mm from the apex. At this point the apparatus in a most preferred embodiment is equipped with additional components to allow devitalization of said tooth canal in which the first electrode is lodged, by applying to it a high energy electric pulse, preferably by applying a current with a power of substantially 70 W RF, at 300 Ω, and a frequency of about 0.5 MHz for about one tenth of a second as also described in e.g. U.S. Pat. No. 6,482,008 B2. This will disintegrate the bundle of nerves (13) and blood in the vein is coagulated at the same time. Practically speaking the whole of the material in the canal is efficiently removed and the canal is sterilized.

Also provided as a second aspect of the invention is a method for determining the location of the apex of a dental root canal, wherein the method comprises the following steps:

(a) providing a first electrode that is located in the root canal of a tooth of a patient and a second electrode which is in contact with another body part of said patient, preferably with the oral mucosa or with a hand of said patient;

(b) carrying out a first fast frequency-sweep comprising:
   obtaining a first series of at least four electrical impedance measurements using the first and the second electrode and using frequencies selected from a frequency of between 10 Hz and 40 kHz, while noting for each individual impedance measurement at which point in time it was taken;

(c) carrying out a second slow frequency-sweep comprising:
   (i) obtaining a second series of at least four electrical impedance measurements using the first and the second electrode and using the same frequency range as defined in step (b) but measuring the individual impedance measurements in slower succession than in step (b), while noting for each individual impedance measurement at which point in time it was taken; or (ii) extrapolating the impedance measurements of the second slow frequency-sweep from the impedance data-set obtained in step (b);

(d) comparing the impedance data-set obtained in step (b) with the impedance data-set obtained in step (c) to determine $t_{max}$ and $\Delta R_{max}$, wherein $t_{max}$ is the common time point in both frequency sweeps at which the impedance difference $\Delta R_{max}$ between an impedance measured at or corresponding to $t_{max}$ in step (b) and an impedance modulus measured at or corresponding to $t_{max}$ in step (c) is largest;

(e) determining the distance x between the apex of said dental root canal and said first electrode using the determined $t_{max}$ and $\Delta R_{max}$ values, as described herein for the apparatus of the invention.

Preferably, in steps (b) and (c) of the method of the invention the same number of impedance measurements are taken. Further preferred is the method of the invention, wherein said frequencies are selected from the frequency range comprising the frequencies between 14 Hz and 10 kHz. In one embodiment, step (b) and/or (c) of the method is/are carried out using a frequency sweep generator. In a preferred embodiment, said extrapolation in step (c) can be carried out by curve fitting of the impedance data obtained from said low frequency sweep in (b) and by rescaling the time values but not the impendence values of said fitted curve. In a further preferred embodiment of the method of the invention in step (d) said largest impedance difference $\Delta R_{max}$ is determined by comparing two impedance curves fitted through the data-set obtained in step (b) and the data-set obtained in step (c), respectively. To determine $\Delta R_{max}$ it may be useful to determine a third curve as described herein above.

In a further aspect the invention provides a computer storage medium comprising a computer-readable program code for implementing the method of the invention or the method used in the apparatus of the invention.

The present invention will now be further described using examples and different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

EXAMPLES

Example 1

The following example can be carried out using an apparatus as described e.g. in EP0392518 B1 with the modification that the apparatus of the invention has to be modified to be capable of carrying out a frequency sweep as described herein above and that the apparatus comprises a computing unit as described herein. Regarding the following examples it is to be understood that the following steps and parameters are only exemplary and not limiting.

Figure 1:
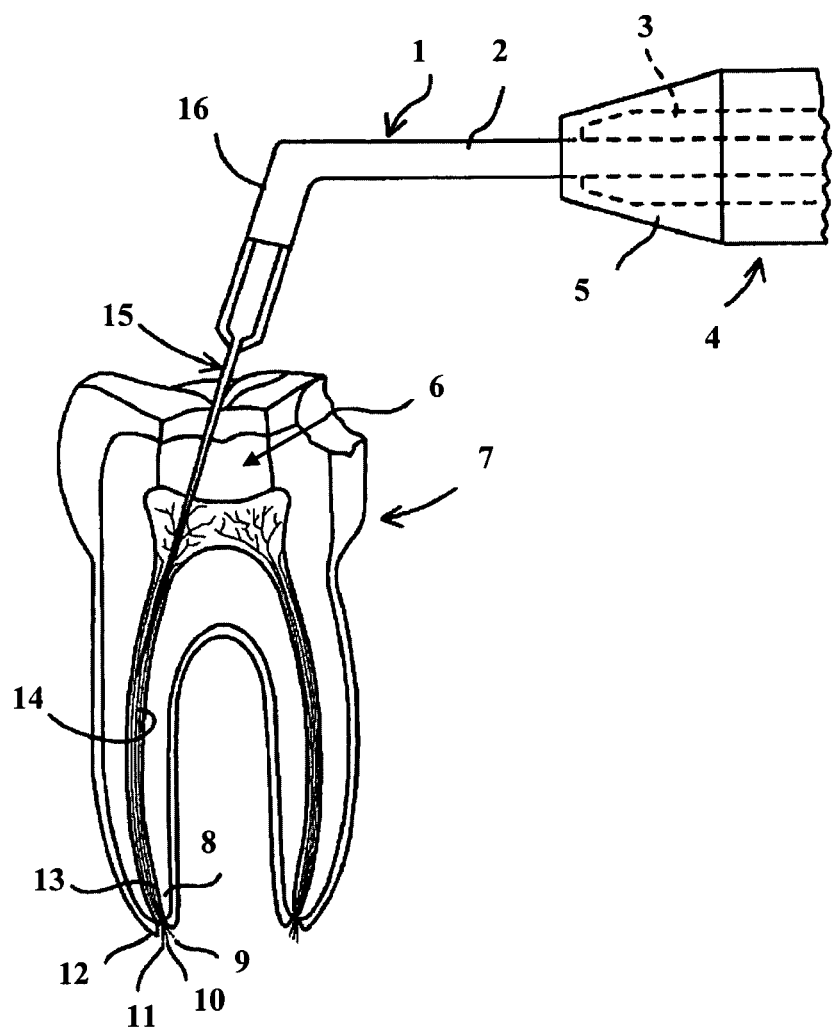
FIG. 1 An illustration showing the insertion of a first electrode, in this example a needle electrode into the root canal of a tooth to determine the distance between the apex of the tooth and the electrode.
Figure 2:
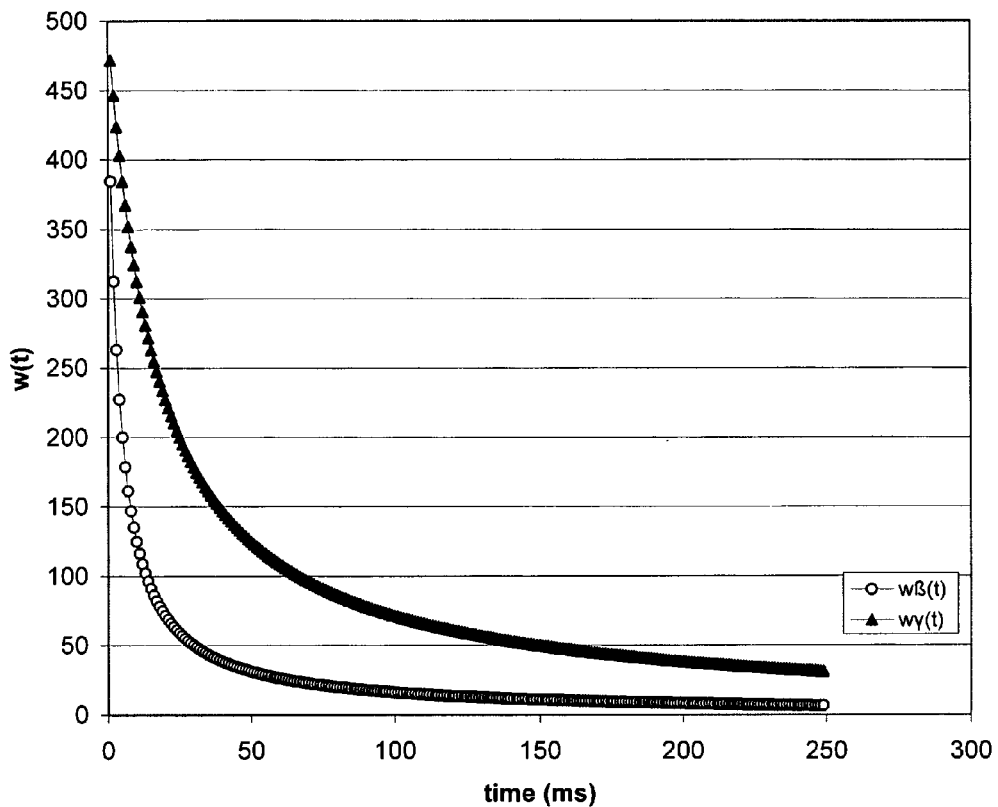
FIG. 2 Exemplary frequency rates are shown which can be used for the succession of voltage signals in the apparatus of the invention.

In a first step, a first electrode which in this example is a needle electrode (15) is inserted into the tooth canal (14). Next the frequency rate γ for the fast first frequency sweep is selected such that the first frequency sweep will be completed preferably within less than 0.6 seconds (see also example 2 below of how to optimize the ratio for the frequency rates β and γ). One exemplary value for γ is shown in FIG. 2. Also shown in FIG. 2 are the parameters and equations that were used for determining the frequencies shown in FIG. 2.

Figure 3:
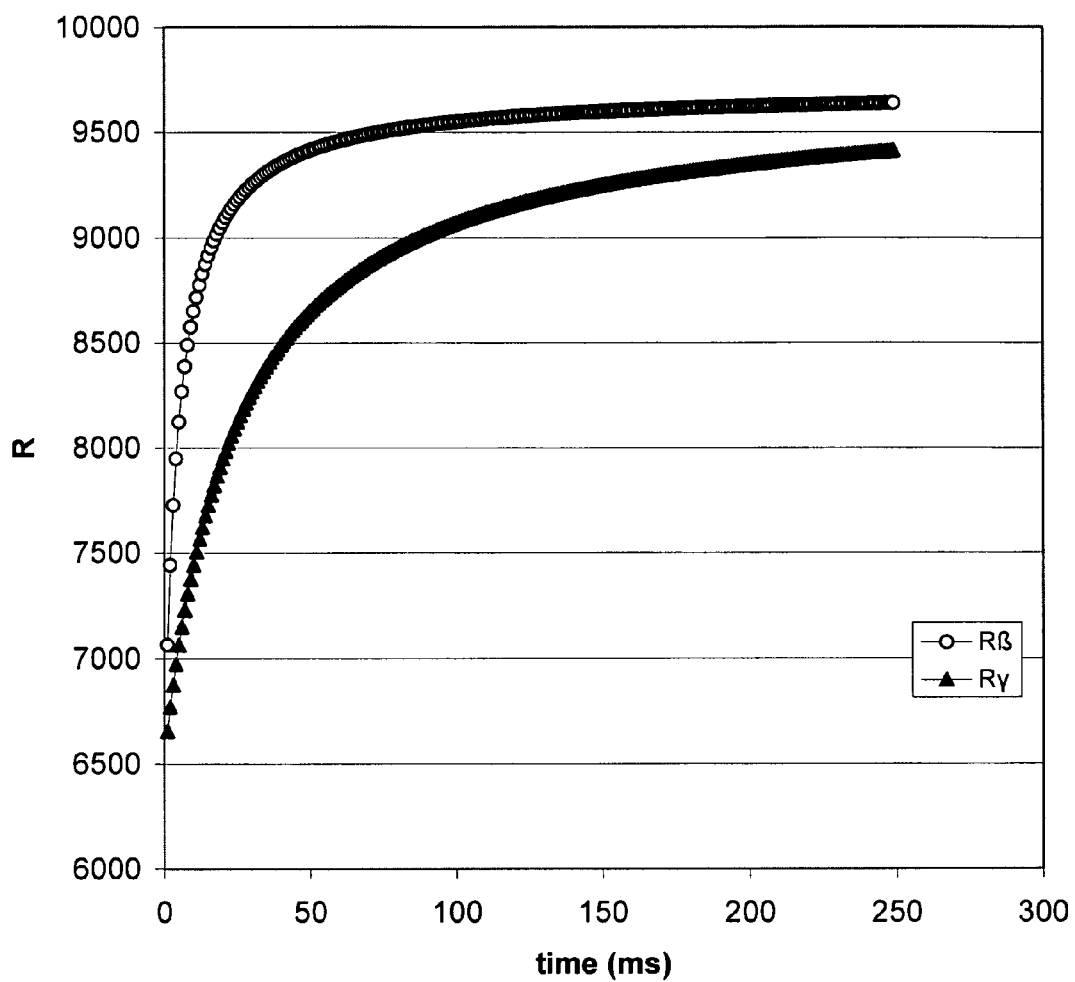
FIG. 3 Exemplary impedance recordings are shown for a given needle electrode position within the root canal, using the frequencies shown in FIG. 2. In this example on the Y-axis the impedance R is shown as recorded voltages.

Next, using the frequency rate γ, the first frequency sweep is carried out using the frequencies shown in FIG. 2. During the sweep, the respective impedance values $R_\gamma$ are recorded and a respective curve is determined ("$R_\gamma$" curve). Exemplary results that can be obtained for the first frequency sweep are shown in FIG. 3.

In a further step, the frequency rate β for the second frequency sweep is selected. β will be ideally selected such that $\Delta R_{max}$ is maximal and $t_{max}$ is less than preferably 0.5 seconds and most preferably less than 0.1 seconds (see also example 2 below). Carrying out the second frequency sweep using β and, in one example the frequencies shown in FIG. 2 for β (i.e. obtained for $w_\beta(t)$), the impedance values $R_\beta$ for the second sweep will be recorded. One possible result for the second sweep is shown in FIG. 3 ("$R_\beta$" curve).

Figure 4:
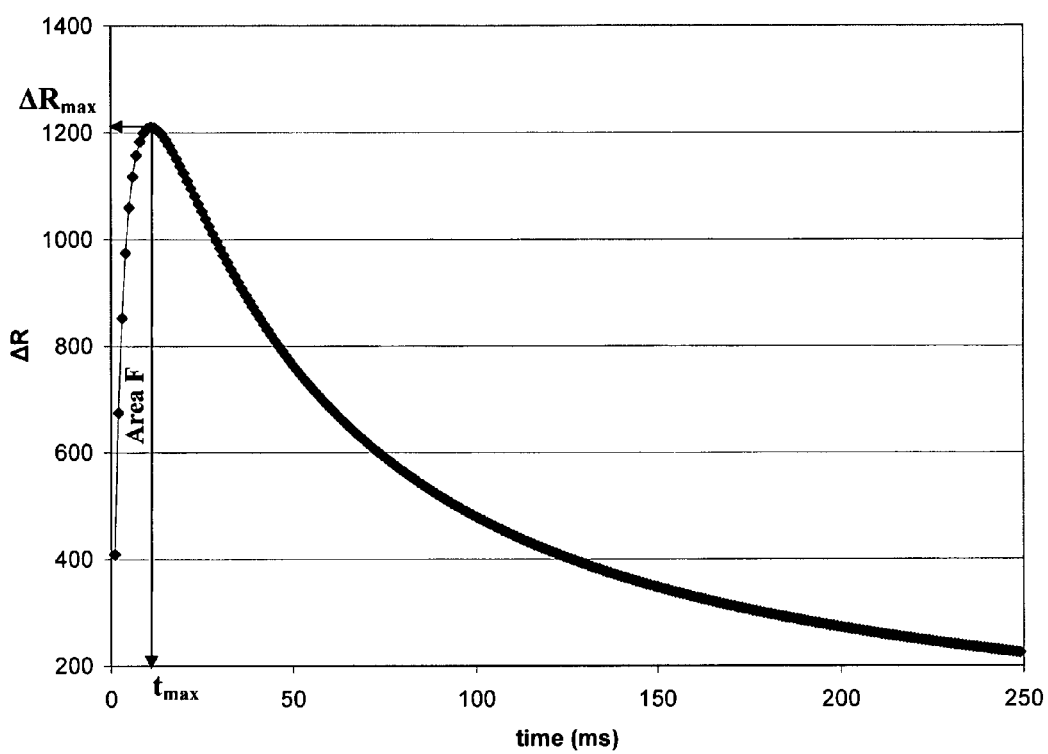
FIG. 4 This example demonstrates how to determine said third curve and $\Delta R_{max}$, $t_{max}$ and the area F under the curve between $t=0$ and $t=t_{max}$ based on the impedance curves $R_\beta$ and $R_\gamma$ shown in FIG. 3.

Next, curves fitted for the recorded impedance values of the first and second frequency sweep will be subtracted from each other, i.e. the curve fitted for the β sweep (curve "$R_\beta$") will be subtracted from the curve fitted for the Rγ values. Preferably, the third curve is derived by the absolute difference between the first and second curve according to $\Delta R=|R\gamma-R_\beta|$. The result, i.e. the third curve, is shown in FIG. 4. Next, $\Delta R_{max}$ and $t_{max}$ are derived from the third curve as also shown in FIG. 4.

It could be shown that in the clinically relevant range, namely when the distance between the first electrode and the tooth apex approaches 2 mm and less, the accuracy of the improved method of the invention is approximately 2-3 fold greater than prior art methods such as the method described in EP 0 392 518.

Using the determined values for $\Delta R_{max}$ and $t_{max}$ the distance between the needle electrode and the tooth apex can be computed e.g. using lookup tables or calibration factors or also by using the following formulas:

$$x_1=a(A+(A^2-1)^{0.5}) \text{ (for } x>A)$$

$$x_2=a(A-(A^2-1)^{0.5}) \text{ (for } x<A)$$

wherein:

$x_{1/2}$ is the distance between the tip of the first electrode (needle electrode in the above example) and the tooth apex;

a=(D−d)/2h; a can be for example 0.00625, if D=0.35 mm und h=20 mm;

b=d/a; b can be for example 16 if d=0.1 mm;

A=(B/$R_o$−1);

B=2*roh/(3.14*d*a); B can be, for example 2*10⁴ Ohm, if roh=620 Ohm*mm;

D=average diameter of the upper end of the tooth canal which is generally between 0.2-0.5 mm;

d=average diameter of the lower end (near the apex) of the tooth canal which is generally between (0.05-0.15 mm);

h=length of the tooth canal, which may be between 16 and 24 mm;

roh=specific electrical resistance of the tooth canal (Ohm*mm²/m) which lies typically between 50-1000 kOhm*mm²/m; and u=ratio of β/γ; optimally u=5.83.

Furthermore, the following relationship can be used to determine the electrical resistance $R_o$: If in one embodiment w=$w_o$/(1+βt) as also outlined above and in FIG. 2, and the capacitive resistance Rc=1/(w*C), wherein C is the tooth-specific capacitance, then R=$R_o$*Rc/($R_o$+Rc). The same applies analogously, if in one embodiment w=$w_o$/(1+γt). Exemplary equations that can be used with the apparatus of the invention including for $R_β$ and $R_γ$ are provided in FIG. 2.

Example 2

Determining the Optimal Frequency Sweep-Rates β and γ.

For selecting the optimal frequency sweep rates γ and β two aspects are to be considered so that the impedance measurements can be carried out with optimal accuracy: On one hand the location of the apex should be carried out as fast as possible to allow a nearly real-time display of the electrode position with respect to the tooth apex. Thus, γ should be selected such that the first frequency sweep is completed sufficiently fast, preferably within less than 0 5, more preferably within less than 0.1 seconds. On the other hand, a second slower frequency sweep will be carried out in a preferred embodiment of the apparatus of the invention using a preferably slower frequency sweep rate β. Thus, if the frequency rate γ has been already preset to a value which is known to work well, i.e. to complete the first sweep in time, then it is convenient to determine the frequency sweep rate β from the relationship β=uγ (as u=β/γ). Thus the ratio u determines how much faster the fast frequency sweep is compared with the slower frequency sweep.

To determine the optimal sweep rate β the following considerations apply for the case when the first frequency-sweep is carried out by selecting the frequencies according to the following formula:

$$w_β(t)=w_o(1+βt)^n;$$

wherein t is the time, $w_β(t)$ is the time-dependent frequency function, $w_o$ is the starting frequency of the sweep, β is the frequency rate (e.g. the rate by which the frequencies are increased or decreased during the first sweep), and n is −1.

From the third curve which is obtainable by subtracting the second curve from the first curve as described also above, i.e. by subtracting the impedance curve $R_γ$ from the impedance curve obtained for the $R_β$ values (an example for said third curve is illustrated in FIG. 4) also F can be determined, which is the area under the third curve between t=0 and t=$t_{max}$. The area F is useful, for example, for determining the impedance $$R_o=2γFu^{0.5}(u^{0.5}+1)/(u^{0.5}-1)$$

The values of $ΔR_{max}$ and $t_{max}$ are dependent on the ratio of the sweep rates, i.e. on u, which is defined as β/γ:

$$ΔR_{max}=R_o^2/(R_o+R_c)(u^{0.5}-1)/(u^{0.5}+1); \text{ wherein } u>1;$$
and $$t_{max}=(R_o+R_c)/R_o/(γu^{0.5}).$$

The larger u becomes, the larger $ΔR_{max}$ will become and also the shorter the time $t_{max}$ will become. This relationship becomes less noticeable for large u values, leading to the question if there is an optimal u, for which the area F (see above and FIG. 4) becomes maximal. This is advantageous as when ΔR(t) curves (i.e. a third curve as exemplified also in FIG. 4) are obtained that are characterized with a maximal area F then the signal-to-noise-ratio of the measurement using the apparatus of the invention will become maximal. This is of particular relevance as this improved noise tolerance will be most noticeable when the first electrode is in close proximity to the tooth apex.

In other words, an optimal measurement using the apparatus of the invention is obtainable when:
(i) the impedance signal ΔR becomes as large as possible, so that it can be separated most effectively from any background noise in the measurement; and
(ii) if the measurement time $t_{max}$ for obtaining the maximum impedance difference $ΔR_{max}$ is as short as possible, so that a result, namely the apex location can be determined in close to real-time.

The area F can be calculated by using the following approximation:

$$F(u)=½ΔR_{max} t_{max}=R_o(u^{0.5}-1)/(u^{0.5}+1) u^{-0.5}/2γ$$

Setting the first derivative dF/du to zero, one can compute for the maximum the optimal value u as follows:

$u_{opt}=(2^{0.5}+1)^2=5.83$ (in this example the following applies for the time dependence of the frequency w(t): n=−1 and, thus, w = $w_o$/(1+βt))

The value for γ is preferably adjusted so that all impedance values are measurable using a cost-effective design of the apparatus of the invention. Having obtained an optimal γ, the sweep rate β for the second frequency sweep can, in one preferred embodiment, conveniently be obtained by the formula: β=γ/u, i.e. in this preferred embodiment, β=γ/5.83.

When the frequency sweep is to be carried out using a different frequency function, e.g. using values for n other than −1 then an optimal u can be computed analogous the above-outlined procedure.

Figure 5:
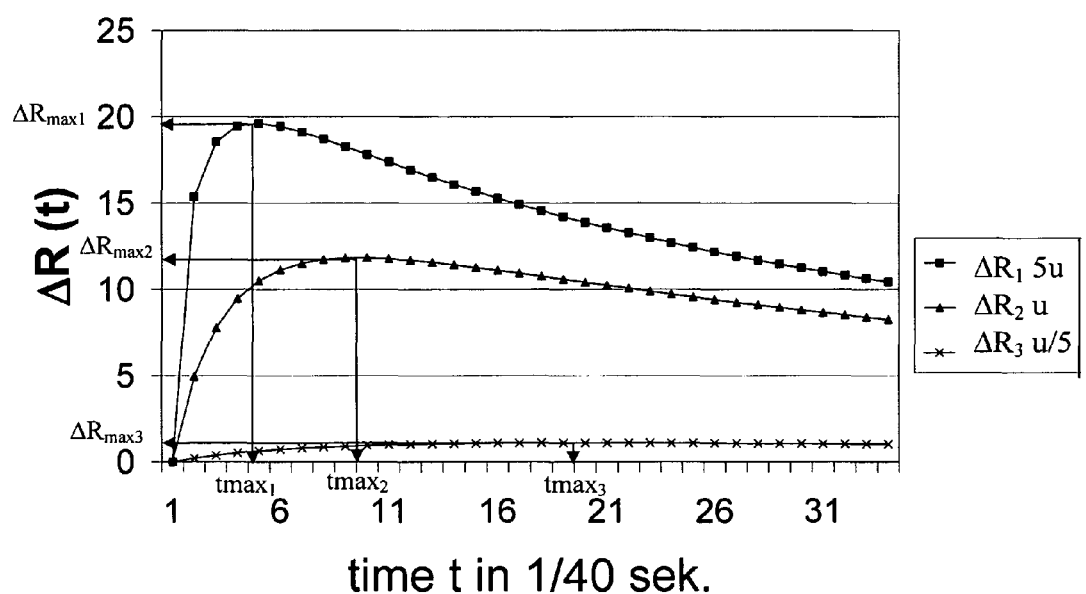
FIG. 5 Shown are impedance measurement curves obtained with three different frequency rate ratios u, namely $u_1=5u_{opt}$; $u_2=u_{opt}$; and $u_3=u_{opt}/5$. The curves shown in FIG. 5 demonstrate how the curve shape and the values for $\Delta R_{max}$ and $t_{max}$ depend on the respective parameter u.
Figure 6:
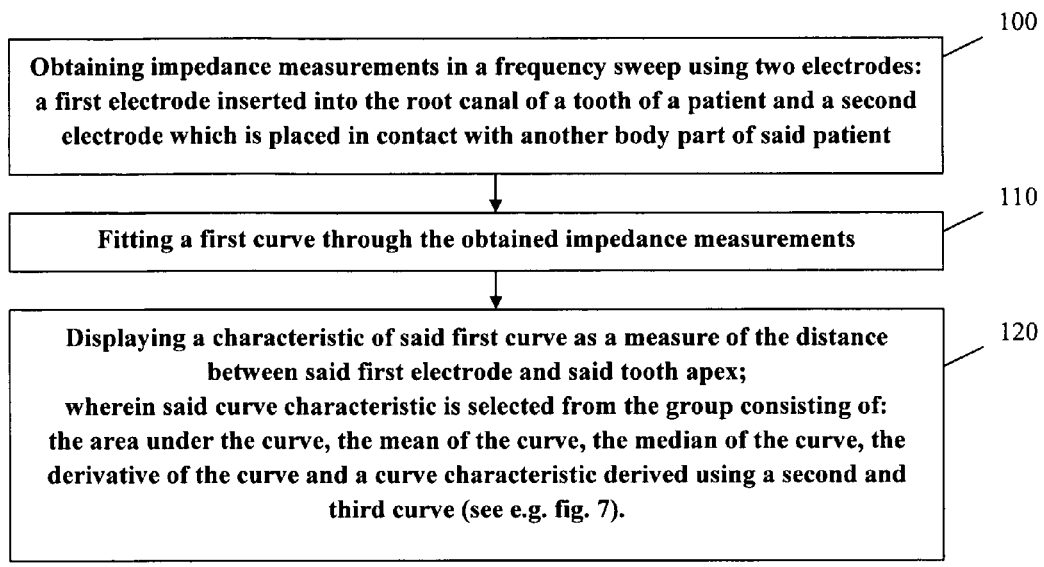
FIG. 6 Flow-chart of a preferred embodiment of determining and displaying the distance between said first electrode and said tooth apex.
Figure 7:
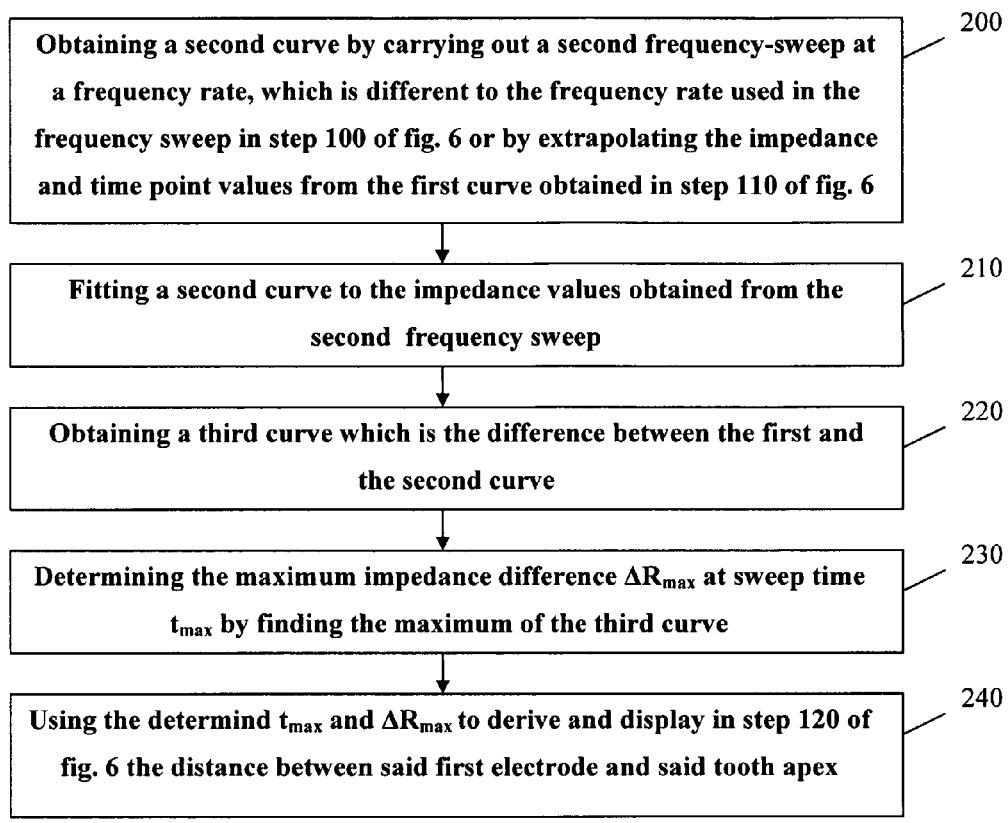
FIG. 7 Flow-chart of a preferred embodiment of step 120 shown in FIG. 6 when using a second and third curve to visualize the relative distance between the apex of the tooth and the first electrode.

FIG. 5 shows exemplary impedance measurement curves obtainable with three different sweep rate ratios u, namely $u_1=5u_{opt.}$; $u_2=u_{opt}$; and $u_3=u_{opt.}/5$. The curves shown in FIG. 5 demonstrate how the curve shape and the values for $ΔR_{max}$ and $t_{max}$ depend on the respective parameter u. The middle curve ($ΔR_2$) as shown in FIG. 5 represents an exemplary result obtainable when using u=$u_{opt.}$=5.83. The other curves shown as $ΔR_1$ and $ΔR_3$ are derived using a u-ratio which is a factor of 5 larger ($ΔR_1$) or a factor of 5 smaller ($ΔR_3$) than $u_{opt}$ of 5.83. As shown in FIG. 5, the values for $ΔR_{max}$ and $t_{max}$ become larger when a larger value is selected for u. However, the area under the curve between t=0 and the respective t=$t_{max}$ becomes largest for u=$u_{opt}$=5.83.

Thus, the following applies:

$$ΔR_{max1}>ΔR_{max2}>ΔR_{max3};$$

$t_{max1} < t_{max2} < t_{max3}$; and $F_1 < F_2 > F_3$; (the respective areas for the curves $\Delta R_1$, $\Delta R_2$ and $\Delta R_3$).

The invention claimed is:

1. An apparatus for determining the location of the apex of a root canal of a tooth, wherein the apparatus comprises the following components:
   (a) a first electrode shaped to be insertable into the root canal of a tooth of a patient and a second electrode which is shaped to be placed in contact with another body part of said patient, preferably with the oral mucosa or with a hand of said patient;
   (b) a frequency sweep generator capable of generating a succession of at least four voltage signals with different frequencies between the first and the second electrode;
   (c) a measuring device capable of measuring the impedances between the first and the second electrode corresponding to the voltage signals generated by said frequency sweep generator;
   (d) a computing unit, capable of:
       controlling the voltage signals generated by the frequency sweep generator;
       reading the respective impedance values from the measuring device; and
       computing the distance between said first electrode and said tooth apex from said impedance values; wherein the computing unit comprises hardware capable of carrying out a method which comprises the following steps:
       (i) carrying out a first frequency-sweep at a frequency rate $\gamma$ and recording for each generated voltage signal the respective impedance value and time point of the impedance measurement; and
       (ii) determining the distance between said first electrode and said tooth apex from the impedance values recorded in (i), and wherein step (ii) comprises fitting a first curve to the impedance values obtained from the first frequency sweep and determining said distance using a curve characteristic of said first curve, or wherein step (ii) comprises the following steps:
           (iii) fitting a first curve through the impedance values obtained from the first frequency sweep, wherein said first curve defines which time points during the first frequency sweep correlate with which respective impedance value of the first sweep;
           (iv) carrying out a second frequency-sweep at a frequency rate $\beta$, which is different to the frequency rate $\gamma$, analogous to (i) or by extrapolating the impedance and time point values from the first curve obtained in (iii);
           (v) fitting a second curve through the impedance values obtained from the second frequency sweep, wherein said second curve defines which time points during the second frequency sweep correlate with which respective impedance value of the second frequency sweep;
           (vi) obtaining a third curve which is the difference between the first and the second curve;
           (vii) finding the maximum of the third curve which is the maximal impedance difference $\Delta R_{max}$ recorded at the time point $t_{max}$; and optionally determining the area F under the third curve between $t=0$ and $t=t_{max}$ and
           (viii) determining the distance x between the apex of said dental root canal and said first electrode using the determined $t_{max}$ and $\Delta R_{max}$ values and optionally the F value, and
   (e) optionally an output device capable of outputting said computed distance.

2. The apparatus according to claim 1, wherein the frequency sweep generator comprises an oscillator and optionally an attenuator.

3. The apparatus according to claim 1, wherein the measuring device comprises an amplifier for amplifying a voltage waveform measured between said first and second electrode.

4. The apparatus according to claim 3, wherein the measuring device comprises a rectifier for rectifying the measured voltage waveform.

5. The apparatus according to claim 1, wherein for the first and second frequency sweep the same number of impedance measurements are taken.

6. The apparatus according to claim 1, wherein the frequencies used in the first and/or second frequency sweep are selected from the frequency range comprising the frequencies between 10 Hz and 40 kHz and more preferably comprising the frequencies between 14 Hz and 10 kHz.

7. The apparatus according to claims 1, wherein the first and/or second frequency-sweep is completed in less than 0.6 seconds and preferably in less than 0.1 seconds.

8. The apparatus according to claim 1, wherein the second frequency-sweep is carried out by selecting the frequencies according to the following formula:

$$w_\beta(t) = w_o * (1 + \beta * t)^n;$$

wherein t is the time, $w_\beta(t)$ is the time-dependent frequency function, $w_o$ is the starting frequency of the sweep, $\beta$ is the frequency rate, and n is any real number.

9. The apparatus according to claims 1, wherein the first frequency-sweep is carried out by selecting the frequencies according to the following formula:

$$w_\gamma(t) = w_o(1 + \gamma t)^n;$$

wherein t is the time, $w_\gamma(t)$ is the time-dependent frequency function, $w_o$ is the starting frequency of the sweep, $\gamma$ is the frequency rate, and n is any real number.

10. The apparatus according to claim 1, wherein the sweep rates $\beta$ and $\gamma$ are selected such that the ratio $u = \beta/\gamma$ is a value between 4 and 8.

11. The apparatus according to claim 1, wherein the first electrode is a needle or reamer electrode preferably having a length of between 10 mm and 50 mm.

12. The apparatus according to claim 1, wherein the second electrode is a lip electrode capable to contact the oral mucosa of the patient and/or a hand-held electrode.

13. A method for determining the location of the apex of a dental root canal, wherein the method comprises the following steps:
   (a) providing a first electrode that is located in the root canal of a tooth of a patient and a second electrode which is in contact with another body part of said patient, preferably with the oral mucosa or with a hand of said patient;
   (b) carrying out a first fast frequency-sweep comprising:
       obtaining a first series of at least four electrical impedance measurements using the first and the second electrode and using frequencies selected from a frequency of between 10 Hz and 40 kHz, while noting for each individual impedance measurement at which point in time it was taken;

(c) carrying out a second slower frequency-sweep comprising:
   (i) obtaining a second series of at least four electrical impedance measurements using the first and the second electrode and using essentially the same frequency range as defined in step (b) but measuring the individual impedance measurements in slower succession than in step (b), while noting for each individual impedance measurement at which point in time it was taken; or
   (ii) extrapolating the impedance measurements of the second slow frequency-sweep from the impedance data-set obtained in step (b);
(d) comparing the impedance data-set obtained in step (b) with the impedance data-set obtained in step (c) to determine $t_{max}$ and $\Delta R_{max}$, wherein $t_{max}$ is the common time point in both frequency sweeps at which the impedance difference $\Delta R_{max}$ between an impedance measured at or corresponding to $t_{max}$ in step (b) and an impedance measured at or corresponding to $t_{max}$ in step (c) is largest; and
(e) determining the distance x between the apex of said dental root canal and said first electrode using the determined $t_{max}$ and $\Delta R_{max}$ values.

* * * * *